United States Patent [19]

Iizuka et al.

[11] 4,433,052

[45] Feb. 21, 1984

[54] PROCESS FOR PRODUCING INTERFERON

[75] Inventors: Masahiko Iizuka, Fujisawa; Hidenobu Kubota, Siga; Emiko Sano, Yokohama, all of Japan

[73] Assignee: Toray Industries, Incorporated, Tokyo, Japan

[21] Appl. No.: 265,369

[22] Filed: May 20, 1981

[30] Foreign Application Priority Data

May 29, 1980 [JP] Japan .................................. 55-70862

[51] Int. Cl.$^3$ ...................... C12P 21/00; C12P 21/02; C12N 5/00
[52] U.S. Cl. ......................................... 435/68; 435/70; 435/240; 435/811
[58] Field of Search .................. 435/240, 68, 70, 811, 435/286; 424/85

[56] References Cited

U.S. PATENT DOCUMENTS

| | | | |
|---|---|---|---|
| 3,773,924 | 11/1973 | Ho et al. | 424/85 |
| 4,007,086 | 2/1977 | Hamilton | 195/1.8 |
| 4,036,693 | 7/1977 | Levine et al. | 195/1.8 |
| 4,189,534 | 2/1980 | Levine et al. | 435/240 |
| 4,266,024 | 5/1981 | Swetly et al. | 435/811 |

OTHER PUBLICATIONS

Dianzani et al; Chem. Abstr. 69:65797j (1968).
Vilcek et al; Chem. Abstr. 78:66844v (1973).
Borden et al; Antimicrobial Agents and Chemotherapy 13, 159 (1978).
Stenesh: *Dictionary of Biochemistry*, J. Wiley & Sons, New York, 1975, p. 188.
Glucocorticoid Hormones Inhibit DNA Synthesis and Enhance Interferon Production in Human Lymphoid Cells Lines, G. R. Adolf and P. Swetly, Nature 282: 736-738 (Dec. 13, 1979).
Growth of Cell Strains on Micro-Carriers in Homogeneous Culture, A. L. vanWezel, Nature 216: 64-65 (Oct. 7, 1967).

*Primary Examiner*—Thomas G. Wiseman
*Assistant Examiner*—James Martinell
*Attorney, Agent, or Firm*—Scully, Scott, Murphy & Presser

[57] ABSTRACT

In producing interferon by treating animal cells proliferated on a microcarrier with an interferon inducer, the cells on the microcarrier are treated with a negatively charged water-soluble macromolecular material.

12 Claims, 3 Drawing Figures

PROCESS FOR PRODUCING INTERFERON

BACKGROUND OF THE INVENTION

This invention relates to a process for producing interferon and more particularly to an improved method for the production of interferon by treating animal cells proliferated on a positively charged microcarrier with an interferon inducer.

Interferon is a protein produced by animal cells by the stimulus of an inducer such as a variety of viruses or double-stranded RNA which is active in inhibiting intracellular proliferation of viruses. Whereas interferon is non-specific for virus species, it is specific for animal species. In other words, an interferon produced with cells of an animal species is not active on another species. In recent years, possible use of interferon as a medicinal has called attention since therapeutic effects of interferon on certain virus diseases and tumors were discovered. In order to achieve application of interferon as a medicinal it is necessary to implement in vitro production, isolation and purification of interferon using a member of human cells. Leucocyte separated from blood was often employed as the cell for producing interferon, but more recently, foetal or neonatal diploid cells have been used instead. Supply of leucocyte necessarily depends upon a group of a large number of non-specified persons, and the interferon products thus prepared will highly possibly be contaminated with various lymphokines. It is therefore difficult to assure safety of the interferon products obtained from leucocyte. On the other hand, as it is easy in the case of the diploid cells to cultivate on a large scale the cells originated from an individual, it is considered that assurance of safety is easilier for such interferon products then for those from leucocyte.

It is known to use a Roux bottle or a roller bottle for the cultivation of anchorage dependent cells such as diploid cells. However, cultivation of a large amount of anchorage dependent cells by such method is considered rather difficult. This is because cultivation on a large scale by this method in which the cells proliferate in monolayer on the bottom of a Roux bottle or on the side of a roller bottle needs a large number of Roux bottles or roller bottles to be handled.

A. L. van Wezel found that animal cells can attach to and proliferate on DEAE Sephadex A50, and named this culture method as microcarrier culture. But DEAE Sephadex A50 has some problems as microcarrier because it has toxic effect on cell growth. D. W. Levine et al improved cell growth by addition of negatively charged polymer such as carboxymethylcellulose to DEAE Sephadex A50 (see U.S. Pat. No. 4,036,693). Further, Levine et al found diethylaminoethylated bridged dextran with lower charge density than DEAE Sephadex A50 is good microcarrier for cultivating anchorage dependent cell and developed a culture method which is suitable for the large-scale cultivation of anchorage dependent cells (see U.S. Pat. No. 4,189,534).

The method consists of inoculating seed cells in a medium composed of a suspended positively charged microcarrier (called microcarrier for short hereinbelow) and carrying out a suspension culture. The inoculated cells attached to surfaces of the microcarrier on which the cells proliferated. The microcarrier culture method readily increases the surface area on which the cells are attached and is easy to handle. The method therefore can be regarded as a culture method quite suitable for the large-scale cultivation of anchorage dependent cells.

In addition to the above-mentioned technique by which interferon is produced in culture cells, there are known a method called superinduction method in which production of interferon is further enhanced by stimulating the cells with an interferon inducer such as double-stranded RNA followed by treatment of the stimulated cells with an antimetabolite such as cycloheximide or actinomycin D (see U.S. Pat. No. 3,773,924) and a method called UV method in which the production of interferon is further enhanced by irradiating the cells with UV light shortly before and/or after the stimulation with an interferon inducer.

It is also known as a priming effect of interferon that treatment of the cells with an interferon at a low concentration stabilizes production of the interferon.

In consideration of the above-described culture and interferon production methods for producing a large amount of interferon from cultured cells such as diploid cells, we carried out a production of interferon by the superinduction method after priming interferon treatment of the cells cultivated by the microcarrier culture method. Such method often produced a low-potency interferon and was not stable in producing a high-potency interferon.

SUMMARY OF THE INVENTION

It is an object of this invention to provide a process for producing interferon which is suitable for large-scale production by overcoming the aforementioned.

Other objects and advantages of the present invention will be apparent from the descriptions hereinbelow.

The above-cited objects of the invention are achieved by, in treating animal cells proliferated on a microcarrier with an interferon inducer for the production of interferon, treating the microcarrier on which the cells have been attached and proliferated with an interferon production-promoting material.

Negatively charged water-soluble macromolecular materials are used as the production-promoting materials. The negatively charged water-soluble macromolecular materials act to increase the efficiency of interaction between the interferon inducer and the cells on the microcarrier and thus are effective in enhancing the production of high potency interferon at a relatively stable rate. They are also effective for contacting the interferon inducer which is an expensive material efficiently with the cells thereby enabling decrease in concentration of the inducer, that is, decrease in amount of the inducer used.

In addition, combination of a negatively charged water-soluble macromolecular material with glucocorticoid may be employed. The negatively charged water-soluble macromolecular material and the glucocorticoid respectively exert an interferon production-enhancing action with the result that synergism is attained.

Glucocorticoid is effective for maintaining the cells on the microcarrier under conditions suitable for the production of interferon, namely, appropriately controlling cytopathy caused by the interferon inducer to stablize production of a high-potency interferon by the cells.

DETAILED DESCRIPTION OF THE INVENTION

The method of cultivating anchorage dependent cells such as diploid cells by using a microcarrier upon which the process of the invention is based will be described below.

A medium containing a microcarrier suspended therein and, as required, serum at an appropriate concentration is inoculated with seed cells and incubated with slow stirring at an appropriate temperature.

As the microcarrier is used a microparticulate matter composed of a polysaccharide such as dextran, dextrin, starch, cellulose or a substituted derivative thereof, or a synthetic polymer such as polyvinyl alcohol, hydroxy-substituted polyacrylate or polymethacrylate or polystyrene with which a positively charged group, for example, an amine group such as diethylaminoethyl or dimethylaminopropyl is combined to an appropriate degree.

Although concentration of the microcarrier may vary depending upon such factors as nature of the microcarrier and nature of the cell to be cultivated, it is preferably in the range such that surface area of the microcarrier per ml. of the medium is from about 10 $cm^2$ to 100 $cm^2$. Composition of the medium and concentration of the serum may be appropriately determined depending upon nature of the cells to be cultivated, concentration of the cells and the like.

The inoculated cells attach to surfaces of the microcarrier, start proliferation, and by continuously cultivating at an appropriate temperature for a period from several days to 10 days, proliferate to such an extent that the microcarrier surfaces are almost completely covered with the cells. During the proliferation, as required, such operations as oxygen supply, pH adjustment, nutrient supplement and medium renewal are performed.

Next, production of interferon by the cells cultivated by the microcarrier culture method will be described in details.

If required, the cell culture prior to interferon induction is incubated in a medium containing a low-potency interferon for a period from several hours to one day to enhance the production of interferon.

The present invention essentially comprising adding a negatively charged water-soluble macromolecular material to a medium in which the microcarrier particles with cells attached and proliferated are suspended at a time when or before an interferon inducer is added.

As the negatively charged water-soluble macromolecular material are preferably employed water-soluble carboxyl-containing macromulecular materials, for example, carboxymethylcellulose (called CMC for short herein below), polyalginate, polyglutamate and pectin, water-soluble phosphate-containing macromolecular materials, for example, cellulose phosphate and water-soluble sulfate-containing macromolecular materials, for example, dextran sulfate and heparin. Preferred concentration and time of addition of such water-soluble macromolecular material may be determined appropriately depending upon nature of the macromolecular material. For example, using CMC which contains carboxyl of a weaker acidity, it is preferred to add an amount corresponding to a concentration from 0.05% to 1%, and more preferably from 0.1% to 0.5% longer than 5 hours, and more preferably longer than 10 hours prior to the addition of an interferon inducer. In the case of dextran sulfate containing sulfate of a stronger acidity, an amount corresponding to a concentration from 0.0001% to 0.01% is preferably added immediately or at longest one hour prior to the addition of an interferon inducer.

As described earlier in U.S. Pat. No. 4,036,693, negatively charged macromolecular material such as carboxymethylcellulose was added to improve cell growth on positively charged microcarrier such as DEAE Sephadex A50. In above case, negatively charged polymer was added before or during cell growth phase to improve cell growth by lowering the positive charge density of the microcarrier.

In our present invention, it is necessary to add the water-soluble macromolecular material after the cells have been attached and proliferated, and the addition should not be made during the proliferation phase, long before the addition of an interferon inducer. For example, Table 1 shows number of the cells produced when 200 ml. of Eagle's MEM medium containing 5% calf serum, CMC at various concentrations and 0.25% diethylaminoethylated bridged dextran microcarrier was inoculated with $2 \times 10^7$ human diploid cells and a cultivation was carried out with stirring at 37° C. for 7 days. As clearly seen from the table, addition of the water-soluble macromolecular material during the cell proliferation phase greatly inhibits proliferation of the cells.

TABLE 1

| CMC concentration, % | Number of the cells, cells/ml. |
| --- | --- |
| 0 | $6.8 \times 10^5$ |
| 0.0125 | $6.1 \times 10^5$ |
| 0.025 | $3.4 \times 10^5$ |
| 0.05 | $2.1 \times 10^5$ |

In order to carry out the process of the present invention particularly effectively, it is preferred to add the above-cited water-soluble macromolecular material prior to the addition of an interferon inducer. However, for water-soluble macromolecular materials of a stronger acidity such as dextran sulfate, the addition may be simultaneously with or after the addition of an interferon inducer with a considerable effect produced. Such embodiment is also covered by the invention.

The glucocorticoid used is hydrocortisone, prednisolone, dexamethasone or the like but is not limited thereto. The concentration of hydrocortisone, predinisolone or dexamethasone is usually in the range from 0.01 to 100 micromoles ($\mu M$) and preferably from 0.1 to 10 $\mu M$. It is preferred to add the glucocorticoid from 72 to 6 hours, particularly 48 hours prior to the addition of an interferon inducer.

Glucocorticoid at a concentration exerting an interferon production enhancing effect increases RNA synthesis without producing any effect upon DNA and protein syntheses.

The interferon production enhancing effect of corticoid is constantly manifested in the microcarrier culture cells, although also it is sometimes apparent in the plate culture cells. In this respect, it is particularly useful in a large-scale production of interferon using microcarrier culture cells. Glucocorticoid is effective for maintaining the cells on the microcarrier under conditions suitable for the production of interferon, more particularly, for appropriately controlling cytopathy caused by the interferon inducer to stabilize production of a high-potency interferon by the cells.

Subsequently, an interferon inducing treatment is performed by a so-called superinduction or UV method.

An interferon inducer is added to a medium in which microcarrier particles with the cells attached and proliferated are suspended. Then, when a superinduction method is used, an antimetabolite such as cycloheximide or actinomycin D is added at an appropriate concentration and on an appropriate time schedule, followed by incubation for an appropriate period of time. The used medium containing the agents as mentioned above is preferably replaced by a fresh medium which is then incubated, for example, for about one day to produce interferon in the medium.

As the interferon inducer which is an agent inducing interferon in the cell are known a wide variety of substances. Among them, the process of the invention is carried out most effectively by using a double-stranded RNA such as poly(I):poly(C), or poly(A):poly(U).

The most preferable concentration of the interferon inducer varies depending upon nature of the cell, nature of the interferon inducer, etc. For example, when poly(I):poly(C) is used as an interferon inducer, a concentration of about 10 $\mu$g/ml. is sufficient for certain cells (human diploid cells). In the process according to the present invention, concentration of the microcarrier, that is, concentration of the cells can be increased to some degrees prior to the interferon inducing treatment to reduce the amounts of the interferon inducer, the antimetabolite and others for an more economical operation. The cultivation, interferon inducing treatment and other procedures are usually operated with stirring and may be in a fluid bed, or if oxygen supply is satisfactory, they may be operated under static condition.

The following examples are illustrative.

EXAMPLE 1

Eagle's MEM medium, 2 l., containing 5% calf serum and 0.25% diethylaminoethylated bridged dextran microcarrier was inoculated with human normal diploid cells at a ratio of $10^5$ cells per ml. An incubation was carried out with slow stirring in a glass spinner flask at 37° C. for 7 days. In the course of the incubation, the culture medium was replaced twice by a fresh Eagle's MEM medium containing 5% calf serum. The cell number attained was $1.05 \times 10^6$ per ml. Then, the medium containing the cells and the microcarrier, each 100 ml., was dispensed in 10 small spinner culture flasks. The cells and the microcarrier were settled, and the supernatant medium was discarded. A medium containing 100 IU/ml. interferon and 2% calf serum was added in an amount equal to the amount of the discarded medium. To a portion of the spinner flasks was added CMC respectively at a predetermined concentration. An incubation was carried out at 37° C. for about 20 hours.

Next, 10 $\mu$g/ml. cycloheximide and a predetermined concentration of poly(I):poly(C) were added respectively. An incubation was performed at 37° C. for 4 hours. Additionally was added 4 $\mu$g/ml. actinomycin D, followed by an incubation at 37° C. for one hour. The cells and the microcarrier were settled, the supernatant medium was discarded and an amount of Eagle's MEM medium equal to the amount of the discarded medium was added. The procedures were repeated once more. Then Eagle's MEM medium containing 0.05% methylcellulose was added. An incubation was then carried out at 37° C. for about 20 hours. The amount of the interferon produced in the finally used medium was measured by the CPE inhibition method using FL cells and vescular stomatitis virus and determined in terms of the international unit. The results are shown in FIGS. 1 and 2.

EXAMPLE 2

Eagle's MEM medium, 2 l., containing 5% calf serum and 0.25% diethylaminoethylated bridged dextran was inoculated with human normal diploid cells at a ratio of $1.5 \times 10^5$ cells per ml. An incubation was carried out in a glass spinner culture flask with slow stirring at 37° C. for 4 days. In the course of the incubation, the culture medium was replaced by a fresh Eagle's MEM medium containing 5% calf serum. Number of the cells thus produced was $6.8 \times 10^5$ per ml. Then, the cells and the microcarrier were settled, and the supernatant medium was discarded. A medium containing 100 IU/ml. interferon and 2% calf serum in an amount equal to the discarded amount was added. An incubation was performed at 37° C. for about 20 hours. Then, the medium containing the cells and the microcarrier, 200 ml. each, was dispensed in 6 small spinner culture flasks. To a portion of the spinner flasks was added dextran sulfate respectively at a predetermined concentration. An incubation was carried out at 37° C. for one hour.

Next, the cells and the microcarrier were settled, the supernatant medium was discarded, an amount of Eagle's MEM medium containing 2% calf serum equal to the discarded amount was added, and then a predetermined amount of poly(I):poly(C) and 10 $\mu$g/ml. cycloheximide were added. An incubation was performed at 37° C. for 4 hours. Then actinomycin D was added and discarded and the incubation was continued to produce interferon in the same way as in Example 1. The amount of interferon thus produced was measured by the inhibition of viral nucleic acid synthesis and determined in terms of the international unit.

The results are shown in Table 2.

TABLE 2

| Concentration of poly(I):poly(U) $\mu$g/ml. | Concentration of dextran sulfate $\mu$g/ml. | Polency of interferon international unit/ml. |
|---|---|---|
| 20 | 0 | 300 |
|  | 10 | 1,500 |
|  | 100 | 900 |
| 50 | 0 | 600 |
|  | 10 | 1,900 |
|  | 100 | 900 |

EXAMPLE 3

Eagle's MEM medium, 1,200 ml., containing 5% calf serum and 0.3% diethylaminoethylated bridged dextran carrier was inoculated with human normal diploid cells at a ratio of $10^5$ cells per ml. An incubation was carried out in a glass spinner culture flask with slow stirring at 37° C. for 5 days. In the course of the incubation, the culture medium was replaced twice by a fresh Eagle's MEM medium containing 5% calf serum. Number of the cells thus produced was $0.9 \times 10^6$/ml. Then, the medium containing the cells and the microcarrier, 200 ml. each, was dispensed in 4 small spinner culture flasks. The cells and the microcarrier were settled, and the supernatant medium was discarded. There were added to one of the flasks a fresh Eagle's MEM medium containing 1 $\mu$M hydrocorticone and 5% calf serum, to another one of the flasks a fresh Eagle's MEM medium containing 1 $\mu$M prednisolone and 5% calf serum and to the remaining two a fresh Eagle's MEM medium containing 5% calf serum, respectively in an amount equal to the amount of the discarded medium. The incubation was continued for an additional day. Then, the cells and the microcarrier were settled, the supernatant medium was discarded, and an amount of a medium containing 100 IU/ml. interferon and 2% calf serum equal to the discarded amount was added. To the flask to which hydrocortisone or prednisolone was added in the previous procedure was added hydrocortisone or prednisolone respectively in such an amount that the same concentration was produced. Additionally, CMC was added to a concentration of 0.2% respectively to three flasks, one with hydrocortisone added, one with prednisolone added and one of the two with no glucocorticoid added. To the remaining one was added no glucocorticoid and no CMC. The incubation of all flasks was continued for an additional 20 hours at 37° C. Then, to all of the flasks were added poly(I):poly(C) to a concentration of 50 μg/ml. and cycloheximide to a concentration of 10 μg/ml. An incubation was carried out at 37° C. for additional 4 hours. Additionally, actinomycin D was added to a concentration of 4 μg/ml. followed by an incubation at 37° C. for an additional hour. The microcarrier with the cells attached was settled, and the supernatant was discarded. Eagle's MEM medium containing 0.2% CMC was then added in an amount equal to the discarded amount. The procedure was repeated once more. Finally, the medium was incubated at 37° C. for about 48 hours. In the course of the incubation, about 2 ml. of the culture supernatant was withdrawn after 24 hours for the measurement of interferon potency. Amounts of interferon produced in the final medium at 24th hour and 48th hour after initiation of the incubation were measured by the CPE inhibition method using FL cells and vesicular stomatitis virus and determined in terms of the international unit.

The results are shown in Table 3.

TABLE 3

Interferon Production-enhancing Effects of Hydrocortisone, Prednisolone and Carboxymethylcellulose (CMC).

| Additive | | | Interferon potency, IU/ml. | |
|---|---|---|---|---|
| Hydrocortisone | Prednisolone | CMC | 24th hr. | 48th hr. |
| − | − | − | 4,000 | 4,800 |
| − | − | + | 6,500 | 8,300 |
| + | − | + | 9,200 | 19,000 |
| − | + | + | 8,000 | 19,000 |

EXAMPLE 4

Eagle's MEM medium, 1.4 l., containing 5% calf serum and 0.3% diethylaminoethylated bridged dextran microcarrier was inoculated with human normal diploid cells at a ratio of $1.5 \times 10^5$ cells per ml. An incubation was carried out in a glass spinner culture flask with slow stirring at 37° C. for 4 days. In the course of the incubation, the culture medium was once replaced by a fresh Eagle's MEM medium containing 5% calf serum. Number of the cells thus produced was $6.8 \times 10^5$/ml.

Next, the medium containing the cells and the microcarrier, 200 ml. each, was dispensed in 7 small spinner culture flask. The cells and the microcarrier were settled, and the supernatant was discarded. To a portion of the spinner flasks was added hydrocortisone respectively at a predetermined concentration. Then, an incubation was carried out at 37° C. for one day. The cells and the microcarrier were again settled, and the supernatant medium was discarded. To the flasks were added interferon to a concentration of 100 IU/ml., calf serum to a concentration of 2% and CMC to a concentration of 0.2%. Additionally, to the flasks with hydrocortisone previously added respectively at a predetermined concentration was added hydrocortisone respective to the same concentration as before. An incubation was then performed at 37° C. for about 20 hours.

Next, to all of the flasks were added poly(I):poly(C) to a concentration of 50 μg/ml. and cycloheximide to a concentration of 10 μg/ml. An incubation was then performed at 37° C. for 4 hours, followed by addition of actinomycin D at a concentration of 4 μg/ml. and an incubation at 37° C. for an additional hour. The microcarrier with the cells attached was settled, and the supernatant was discarded. Eagle's MEM medium containing 0.2% CMC was added in an amount equal to the discarded amount. The procedures were repeated once more. The final medium was incubated at 37° C. for additional about 48 hours. The amount of interferon produced in the final medium in 48 hours was measured by the CPE inhibition method using FL cells and vesicular stomatitis virus and determined in terms of the international unit.

BRIEF DESCRIPTION OF DRAWINGS

In FIG. 1 the x-axis is concentration of poly(I):poly(C) in μg/ml. and the y-axis potency of interferon in IU/ml. Interferon production wherein concentration of carboxymethylcellulose added is 0.25% is marked circle and the one in which it is 0% is marked triangle.

FIG. 2 indicates interferon production wherein concentration of poly(I):poly(C) added is 10 μg/ml. In the figure, the x-axis is concentration of carboxymethylcellulose added in %, and the y-axis potency of interferon.

Figure 1:
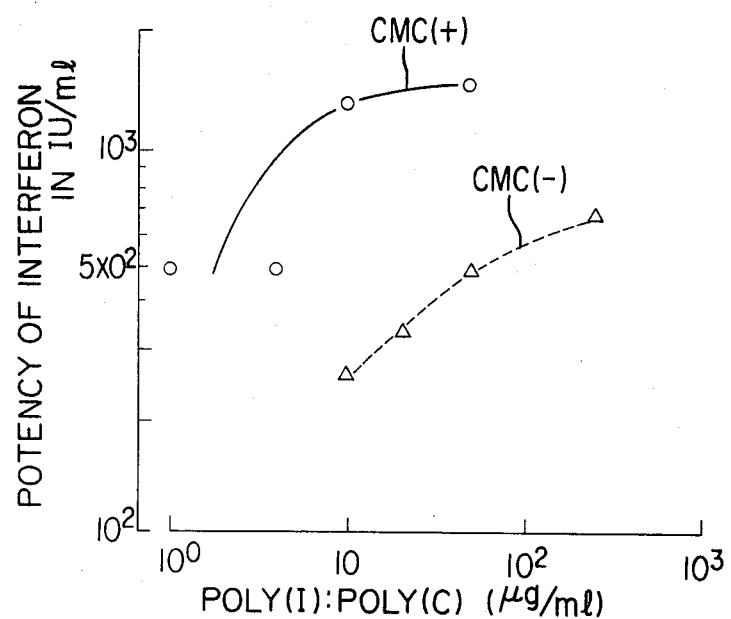
FIGS. 1 and 2 show the results of Example 1.
Figure 2:
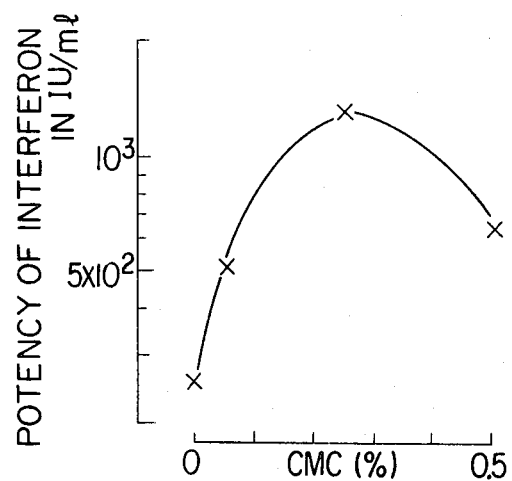
Figure 3:
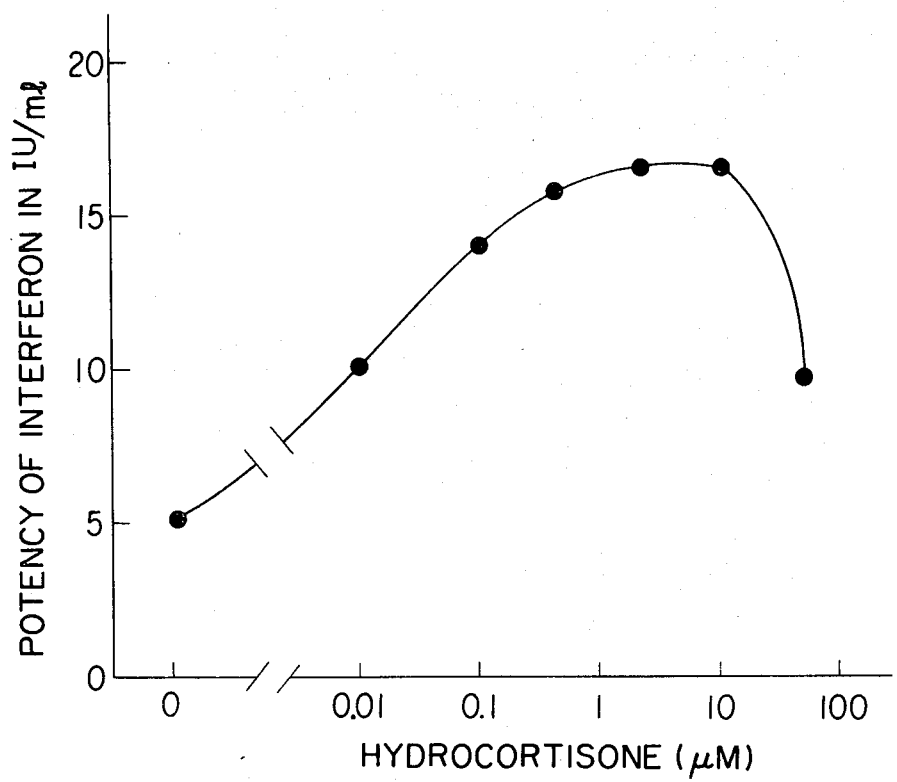
FIG. 3 shows the results of Example 4. The x-axis is concentration of hydrocortisone in μM, and the y-axis potency of interferon in IU/ml.

What is claimed is:

1. A process for producing interferon by treating animal cells proliferated on a positively charged microcarrier which comprises treating said proliferated cells, either before or before and during treatment of the cells with an interferon inducer, with a negatively charged water-soluble macromolecular material selected from the group consisting of carboxymethyl cellulose, polyalginate, polyglutamate, pectin, cellulose phosphate, dextran sulfate, and heparin, maintaining said treated cells under conditions suitable for the production of interferon, and recovering interferon.

2. A process according to claim 1 wherein said negatively charged water-soluble macromolecular material is carboxymethylcellulose.

3. A process according to claim 1 wherein said negatively charged water-soluble macromolecular material is dextran sulfate.

4. A process according to claim 1 wherein said treatment is made with a combination of said negatively charged water-soluble macromolecular material with a glucocorticoid material.

5. A process according to claim 4 wherein said glucocorticoid material is a member selected from the group consisting of hydrocortisone, prednisolone, dexamethasone and mixtures thereof.

6. A process according to claim 1 wherein the positive charge on said microcarrier is based upon diethylaminoethyl or diethylaminopropyl group.

7. A process according to claim 1 wherein said positively charged microcarrier is diethylaminoethylated bridged dextran particles.

8. A process according to claim 1 wherein said positively charged microcarrier is diethylaminoethylated bridged dextran particles and density of the diethylaminoethyl group is in the range from 0.1. to 4.5 millimolar equivalents per g. of dried microcarrier.

9. A process according to claim 1 wherein said animal cells are human cells.

10. A process according to claim 1 wherein said animal cells are human diploid cells.

11. A process according to claim 1 wherein said interferon inducer is a double-stranded RNA.

12. A process according to claim 1 wherein said interferon inducer is a polyriboinosinic acid:polyribocytidylic acid complex.

* * * * *